United States Patent [19]
Ebert

[11] Patent Number: 5,154,188
[45] Date of Patent: Oct. 13, 1992

[54] METHOD AND DEVICE FOR DIVIDING EMBRYOS

[75] Inventor: Karl M. Ebert, Millbury, Mass.

[73] Assignee: The Wolf Foundation, Worcester, Mass.

[21] Appl. No.: 697,415

[22] Filed: May 9, 1991

[51] Int. Cl.$^5$ .............................................. A61B 19/00
[52] U.S. Cl. ........................... 128/898; 606/126; 422/102; 435/296; 128/897
[58] Field of Search .............................. 600/33–35; 604/906; 606/126; 128/749, 751, 897–898; 99/506–508, 509–513; 800/2, DIG. 6; 435/172.2, 172.3, 296; 119/6.5, 6.6, 6.8; 422/72, 99, 102

Primary Examiner—C. Fred Rosenbaum
Assistant Examiner—C. Maglione
Attorney, Agent, or Firm—George C. Atwell; Clarence L. Carlson

[57] ABSTRACT

An apparatus for dividing embryos that are maintained in a flushing or saline solution is provided for removable insertion within a test tube-like container having an open container end and a sealed rounded end. The apparatus assembles within or without the container and includes a generally cylindrical partition cup having a rounded end that conforms to the rounded sealed end of the container and an elongated cylindrical central barrel having an elongated chamber, the central barrel having a portion thereof which is placed contiguous to the partition cup. The apparatus also includes an elongated, generally cylindrical embryo guide funnel having a funnel-shaped end further defined by an elongated member. The elongated member further defines a tubular passageway that allows the embryo to pass therethrough for division or bisection by a cutting edge attached to the partition cup and positioned adjacent the passageway. The apparatus can be used with a centrifugal method or a negative pressure method to force or propel the embryo through the passageway and against the cutting edge in order to divide the embryo in half. A pair of embryo holding chambers formed within the partition cup are adapted to hold each half of the divided embryo until transfer to a recipient as part of the process of genetically improving livestock and other animals.

16 Claims, 3 Drawing Sheets

METHOD AND DEVICE FOR DIVIDING EMBRYOS

BACKGROUND OF THE INVENTION

It has been known for almost a century that embryo transfer is one tool for assisting in the genetic improvement of livestock. Embryo transfer occurs after embryo division, and the ultimate result is the production of twin animals having similar and enhanced genetic qualities. For example, naturally occurring twin bovine offspring are generally regarded as undesirable and are infrequently genetically identical. In addition, if the twin offspring consists of a male and a female, the male influences the female to such a degree as to produce a sterile female called a freemartin. However, twin bovine offspring produced by embryo splitting and embryo transfer are distinct from naturally occurring twins in that they both have the same sex and do not suffer the disadvantages of sterility. Among the advantages of embryo splitting as the preferred form of bovine cloning are more pregnancies per donor recovery and the absence of long-term culture (5-7 days) of the bovine embryo prior to transfer to a recipient. This can also provide a quicker return on investment by reducing the cost of embryo transfer, and allowing half of the embryo to be transferred and half to be used in sexing (splitting only female embryos) or freezing.

Since the 1970's embryo splitting and embryo transfer have become an established practice in livestock production.

Techniques for embryo splitting and embryo transfer originated with work on laboratory animals. Because the size of the embryos undergoing division are often between 70 and 150 microns in diameter, the precision manipulations on the embryos are referred to as micromanipulations.

Experimentation over the last two decades has resulted in the utilization of a number of different techniques for dividing embryos. Common to all techniques are at least four essentials:
1) a medium for maintaining the embryos during micromanipulation;
2) a means of holding the embryo;
3) a means for holding the micro-instrument(s) used in embryo division; and
4) a controlled means of bringing the embryo and the micro-instrument(s) together.

A common holding medium is a phosphate-buffered saline (PBS) medium. Included in this medium may be one to ten percent of heat-treated fetal calf serum (FCS). In addition, antibiotics such as penicillin, streptomycin, or amphotericin are added as well as physiological concentrations of glucose or sodium pyruvate. The embryos and the maintaining medium are contained in a sterile, plastic petri dish, and the micromanipulations on the embryo(s) are performed while they are maintained in the petri dish or on a depression slide.

Several key terms which occur in the micromanipulation of embryos should be defined for the purpose of clarity and understanding. The term "embryo" is a loose term and connotes any of the various early developmental stages of mammals. Depending on the circumstance, the "embryo" could denote a zygote, a morula, or a blastocyst. The zona pellucida is the acellular glycoprotein material that forms around the oocyte in the ovary and continues to surround the embryo until the blastocyst hatches from it. Embryos that reach the 16-cell stage begin to resemble mulberries and are called morulae. A blastomere—or cleavage cell—is one of the cells into which the egg divides after fertilization, and a blastocyst consists of an inner cell mass and a thin outer trophoblast layer, the blastocyst being a modified early stage of embryo development. Furthermore, there are generally three categories of embryo division:
1) blastomere separation wherein the early cleavage stage blastomeres are not firmly bound one to another;
2) division of pre-compaction morulae wherein the zona pellucida is opened by a fine glass needle or a horizontal blade, and the morula is expelled or withdrawn by an aspiration pipette. The withdrawn morula are then inserted into a surrogate zona pellucida; and
3) division of post-compaction morulae and blastocysts wherein either the blade or needle method is employed to divide the embryo while it is in the zona pellucida or after it has been withdrawn.

Several different methods for dividing embryos are practiced in medical laboratories, research facilities, and veterinary practices. The micromanipulators are the pieces of equipment or devices which allow the precision, superfine manipulation of the micro-instruments used for dividing embryos, i.e., the microneedles and/or microblades used for embryo dividing. Pneumatic, slide-rail, sliding, and electrically-controlled wormgear are among the various kinds of micromanipulators currently in use.

One method to divide an embryo is to hold it by suction against a fire-polished holding pipette. The holding pipette is controlled by a micromanipulator, and the suction is such that the zona pellucida bulges slightly into the holding pipette. On a second micromanipulator, immediately adjacent the micromanipulator carrying the holding pipette, is the instrument for dividing the embryo. The instrument can be a superfine needle for opening the zona pellucida and dividing the embryo or a horizontal blade glued to the outside of a glass pipette or a vertical blade glued inside the lumen of capillary tubing. The micromanipulator carrying the instrument for splitting the embryo must be of extremely high quality since the movements of the instrument are on the micron range. Then, with the embryo secured by the holding pipette and located near the bottom of the petri dish, the embryo is divided by the lateral movement of the vertical blade or the downward movement of the horizontal blade. Each half of the bisected embryo, now referred to as a "half embryo" or "demi-embryo", is then immediately transferred to a fresh holding medium with, for example, a sterile Pasteur pipette.

The embryos can also be immobilized on a slide surface or on the bottom of a petri dish instead of being held with suction by a holding pipette. In addition, a stereomicroscope or a compound microscope with a magnification potential of 100× is also used to assist the researcher in splitting the embryo. Since embryos can be 70 to 150 microns in diameter, the unaided eye would be completely unable to guide the instruments carried by the micromanipulator for embryo splitting.

Another method of dividing embryos is by using a pivoting microscalpel blade with a cutting edge 10 to 30 microns thick carried on, and secured to, a micromanipulator. With this method the zona pellucida is cut open by a pair of glass microneedles, then a micropipette is inserted through the slit, and the embryo is ejected by dispersal of a small volume of a medium into the zona pellucida. A microscalpel then bisects the embryo (in its blastocyst stage) along its sagittal plane. Each half embryo (demi-embryo) is then placed in an empty zona pellucida (which has been opened and emptied of its embryo prior to embryo splitting) by a micropipette using the aforementioned technique.

Among the factors affecting the ultimate viability of the embryo after division is the quality of the embryos chosen for splitting and the skill in operating the micromanipulators and the micro-instruments to achieve properly bisected embryos. Embryos should have a large number of viable cells and be in the late morula or early blastocyst stage. In achieving proper embryo bisecting, acute skill in using the aforementioned instruments is critical and vital for the procedure to be executed successfully.

SUMMARY OF THE INVENTION

The present invention comprehends an apparatus for dividing embryos by placing the apparatus in a test tube-like container having an open end and a rounded, sealed end, and subjecting the apparatus holding the embryos maintained within a flushing or saline solution to centrifugal forces or negative pressure in order to propel the embryos against a structural component of the apparatus which causes the division or bisection of the embryos.

A preferred embodiment of the apparatus of the present invention includes a three-piece assembly which is placed within the container and press-fitted together in sealable contiguous contact. The apparatus can also be assembled outside the container and then placed therein.

The apparatus includes an elongated, cylindrical embryo guide funnel that, when disposed in its operative position within the container, is located adjacent to the open end of the container. The embryo guide funnel has an open end for receiving the embryos which are suspended in a flushing or saline solution, and an elongated bore wherein the embryos and the solution are temporarily maintained before bisection or division occurs.

Opposite the open end of the embryo guide funnel is a sloping funnel-shaped end which is further defined by an elongated member having a tubular passageway. The tubular passageway allows the embryo to pass through for division or bisection. When disposed in its operative position, the elongated member projects downward toward the sealed end of the container.

The apparatus of the present invention also includes an elongated, cylindrical central barrel which has a first open end, an oppositely-disposed second open end and an elongated chamber extending from the first open end to the second open end. When disposed in its operative position, a portion of the central barrel adjacent the first open end contiguously encompasses a portion of the embryo guide funnel.

The third structural component in the three-piece assembly is a generally cylindrical partition cup having a circumferential inner cup surface and an oppositely-disposed outer cup surface. The partition cup has a rounded end disposed adjacent to the rounded sealed end of the container. In addition, the partition cup includes an integrally formed partition member that projects upward away from the rounded end and toward the funnel-shaped end of the embryo guide funnel when the partition cup and the guide funnel are disposed in their operative position within the container. The partition member, in effect, bisects the partition cup in half by vertically extending the diameter of the partition cup for sealable attachment to opposite sides of the inner cup surface.

The bisection of the partition cup by the partition member creates two separate and isolated embryo holding chambers, one on either side of the partition member. Each chamber is a sterile environment for holding a half portion of an embryo after the embryo has been divided.

The partition member includes a tapered partition edge integrally formed from the partition member and generally located at the apex of the upwardly-projecting partition member. The partition edge juts above the cylindrical partition cup and is located adjacent the tubular passageway of the funnel-shaped end when the apparatus is assembled and disposed within the container.

Several types of severing means are utilized for dividing or bisecting the embryo in half. One severing means includes a removably securable cutting edge mounted to the partition edge and located immediately adjacent to the tubular passageway of the elongated member so that the cutting edge bisects the exit end of the passageway. After an embryo is forced through the passageway it immediately strikes the cutting edge and is thus divided, with each half of the embryo falling into each respective embryo holding chamber.

Another severing means includes a microthin wire spaced a minute distance from the apex of the tapered partition edge, the microthin wire bisecting the exit end of the passageway and extending parallel to the partition edge.

The microthin wire would be attached to opposite sides of the central barrel or the partition cup. As the embryo exits the passageway, it is immediately bisected or divided by the microthin wire. The microthin wire is spaced a minute distance (in microns) from the apex of the tapered partition edge so that there is little, if any, chance that the embryo or the zona pellucida (within which the embryo is enclosed) would partially envelope or wrap around the microthin wire. Moreover, the forceful discharge of the embryo through the passageway, by any of several methods (centrifugal force or negative pressure), or by an injecting means, will facilitate the clean bisection of the embryo by the microthin wire.

When the apparatus for dividing embryos is disposed in its operative position in any one of a number of variously sized containers, the partition cup is the first piece of the apparatus inserted into the container adjacent the rounded end of the container.

The partition cup includes a plurality of spaced-apart projecting cup lands integrally formed from the outer cup surface. The projecting cup lands abut the inner surface of the container adjacent the rounded end and provide an air shell between the partition cup and the inner container surface.

Located generally halfway up on the outer cup surface of the partition cup is a circumferential cup ledge adapted to receive the central barrel which would be the next structural component inserted into the container during internal assembly of the apparatus within the container. The portion of the central barrel adjacent the second open end contacts and rests upon the cup ledge.

Lastly, the embryo guide funnel would be inserted into the container. The embryo guide funnel has a slightly greater thickness adjacent its open end than at the funnel-shaped end, and thus a circumferential funnel ledge is formed where the change in thickness occurs.

When the embryo guide funnel is inserted into the container, the upper cylindrical portion of the embryo guide funnel located between the funnel-shaped end and the funnel ledge is placed inside and in sealable contiguous contact with the central barrel adjacent the first open end. The rim of the central barrel at the first open end abuts the funnel ledge of the embryo guide funnel. Spaced-apart protruding guide funnel lands on the embryo guide funnel project out from the embryo guide funnel and abut the inner container surface, thus providing clearance of the embryo guide funnel from the inner container surface. An air shell is thus created between the embryo dividing apparatus and the container by the clearance provided by the cup lands and the guide funnel lands. By press-fitting the partition cup, the central barrel and the embryo guide funnel together inside the container, a sealed apparatus for dividing embryos is also provided.

It is an objective of the apparatus of the present invention to provide a three piece assembly which can be externally press-fitted together or press-fitted together inside a test tube-like container, and adapted for easy removal therefrom for facilitating cleaning, embryo removal, sterilization and repair.

Another objective of the present invention is to provide an apparatus for dividing embryos which does not require the precision skill and training needed in working any of the various types of micromanipulators well known in the field.

Yet another objective of the present invention is to provide an apparatus which would obviate the need for obtaining zonae with their contents removed, freezing the zonae, thawing the zonae at room temperature, and, after embryo division has occurred by utilizing the apparatus of the present invention, removing each half embryo from each embryo holding chamber and, in a separate procedure, placing each half embryo in a previously frozen zona. The severing means of the present invention will cause each half embryo to be housed in its own zona pellucida after bisection or division, thus obviating the need to transfer the half embryos into previously frozen zonae These and other objects of the invention will become more fully apparent by reference to the appended claims and as the following detailed description proceeds in reference to the various figures of the drawings.

DETAILED DESCRIPTION OF THE PREFERRED EMBODIMENT

Figure 1:
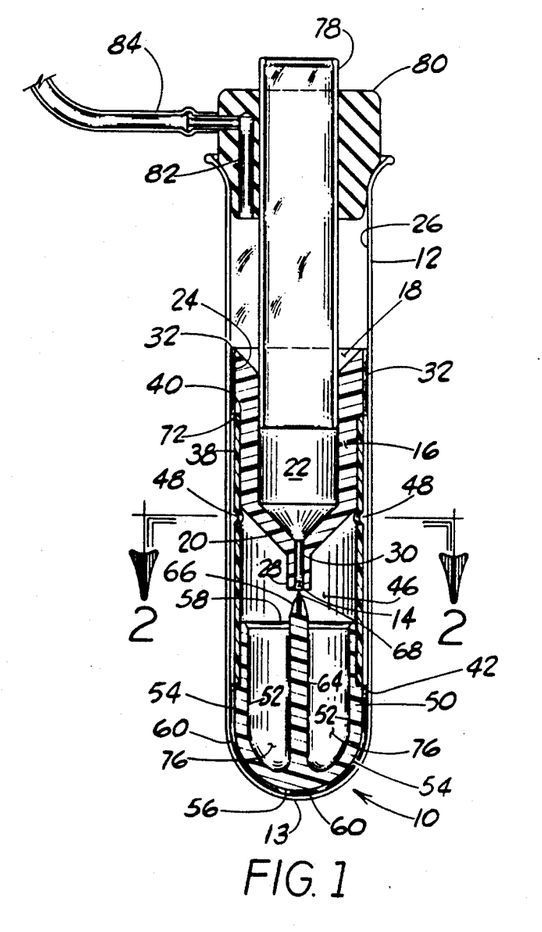
FIG. 1 is a side elevational view of the preferred embodiment of the apparatus of the present invention.

FIGS. 1 through 5 illustrate the preferred embodiment of the embryo dividing apparatus 10 of the present invention. The apparatus 10 is a three-piece assembly, preferably manufactured by a plastic molding process, which is used for dividing embryos suspendedly maintained within a flushing or saline solution (the vehicle medium). The apparatus 10 can be utilized for dividing either one embryo or a number of embryos in succession; in either case, they will be maintained in a vehicle medium. As this description proceeds, the term "embryo(s)" when used will denote either one or a number of embryos. The divided embryos are then transferred to a recipient as part of the process of improving various types of livestock through genetic manipulation. Conceivably, the apparatus 10 could be used to divide embryos of a variety of animals in addition to livestock. The apparatus 10 may be assembled within any of variously sized sterile, test tube-like containers having an open end and a rounded sealed end; or the apparatus 10 may be assembled externally and then placed within the container: in either case the apparatus 10, as shown in FIG. 1, snugly and closely fits within a container 12 and one piece of the assembly conforms to, and is positioned adjacent with, a rounded sealed end 13 of the container 12. Variously-sized ceramic ware and glassware common to all hospitals, medical laboratories, and research facilities may be used as the container in which the apparatus 10 is placed.

The apparatus 10 is adapted for removable placement within any one of these variously-sized containers so that cleaning, repairing, and performing general maintenance on the apparatus 10 can be accomplished quickly and easily. The surfaces of the apparatus 10 must be flawlessly smooth and sterilized before embryo division can occur. Because the diameter of a mammalian embryo may range between 70 to 150 microns, tolerances for the various surfaces of the apparatus 10 must be at least to the hundredth or thousandth of an inch (or metric equivalents), and possibly even smaller. This is necessary so that microscopic burrs, ridges, recesses, pits, etc., are not formed on any of the various surfaces of the apparatus 10 during manufacture. Such flaws, however minute, could interfere with and impede the process of embryo division.

The various structural components of the preferred embodiment of the apparatus 10 and an alternate embodiment of the apparatus, and their particular functions will be described as well as several methods or procedures for dividing embryos.

Figure 5:
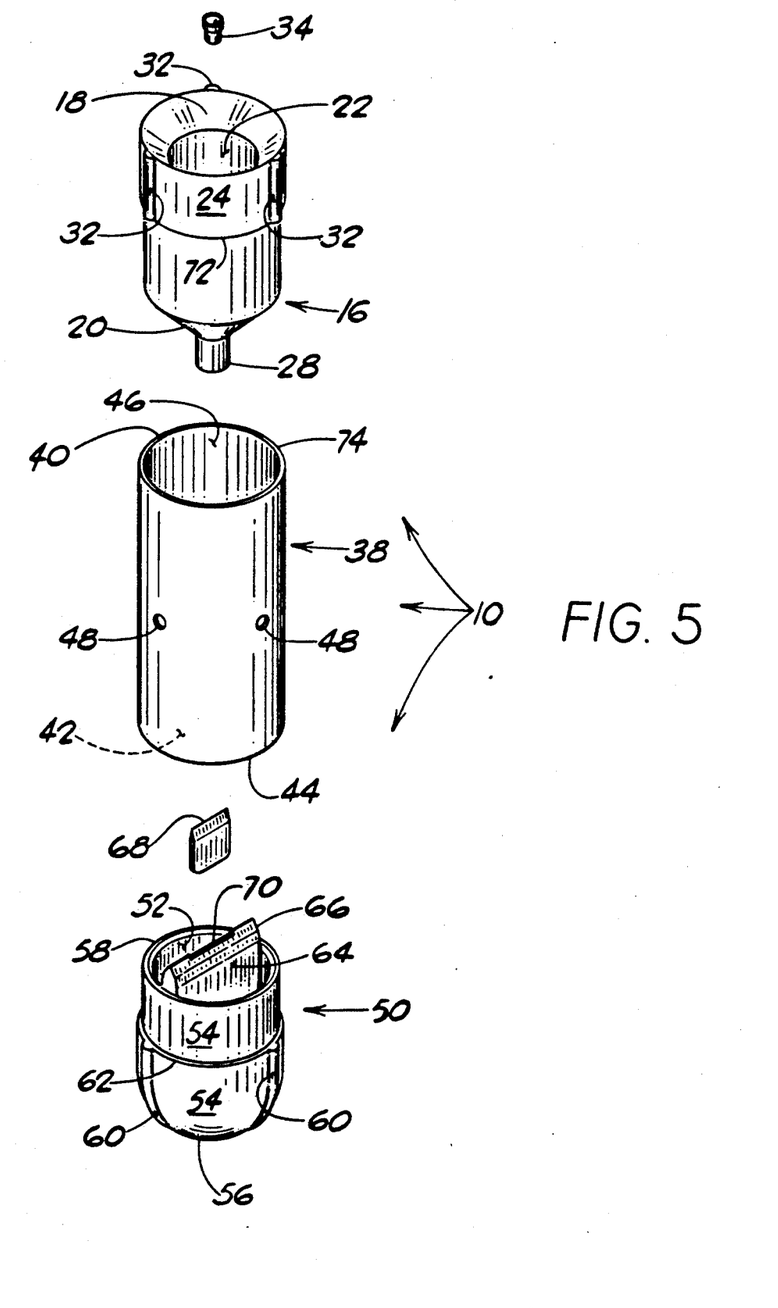
FIG. 5 is a perspective view of the various structural components of the apparatus first shown in FIG. 1.

As illustrated in FIGS. 1 and 5, the apparatus 10 of the present invention includes three separate structural components which can be press-fitted together either within or without the container 12 for dividing an embryo 14. The apparatus 10 includes an elongated, cylindrical embryo guide funnel 16 having an open end 18, an oppositely-disposed funnel-shaped end 20, and an elongated bore 22 extending from the open end 18 to the funnel-shaped end 20. When disposed in its operative position, the guide funnel 16 has a portion of its outer surface 24 at the open end 18 adjacent to an inner surface 26 of the container 12 and an upper cylindrical portion of the funnel-shaped end 20 disposed in contiguous, sealable contact within another structural component to be described more fully hereinafter. The inner surface of the guide funnel 16 adjacent the open end 18 is not sheer, but instead slopes inward toward the elongated bore 22.

Figure 3:
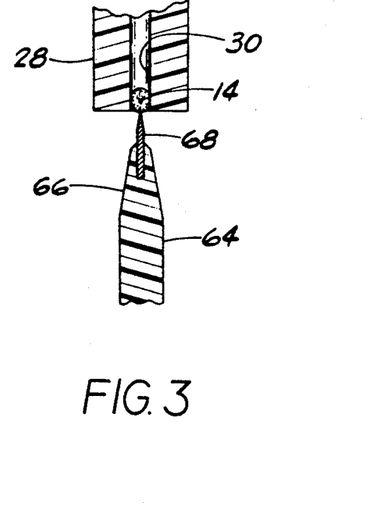
FIG. 3 is an enlarged fragmentary elevational view of part of the apparatus first shown in FIG. 1.
Figure 4:
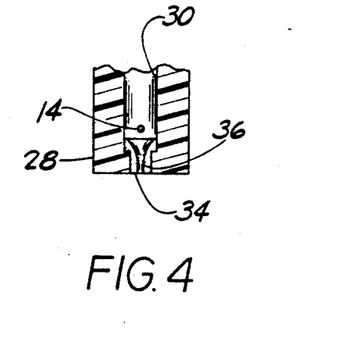
FIG. 4 is an enlarged fragmentary elevational view illustrating a structural addition to the apparatus first shown in FIG. 3.

The funnel-shaped end 20 projects downward toward the sealed end 13 of the container 12 when the guide funnel 16 is disposed in its operative position, and the funnel-shaped end 20 further defines at its tip an elongated, cylindrical member 28 having a tubular passageway 30 extending therethrough as shown in FIGS. 1, 3, and 4. The elongated member 28 also projects downward toward the sealed end 13 of the container 12 when the guide funnel 16 is disposed in its operative position, and the tubular passageway 30 of the elongated member 28 is in flow communication and concentric with the elongated bore 22. Since the diameter of an embryo ranges from approximately 70 to 150 microns, the tubular passageway 30 of the elongated member 28 will have a diameter generally equal to or slightly larger than the embryo 14. Furthermore, the tubular passageway 30 is adapted to receive the embryo 14 or a succession of embryos maintained within the elongated bore 22 and to allow the embryo(s) to pass downward therethrough.

In addition, as illustrated in FIGS. 1 and 5, the guide funnel 16 includes a plurality of longitudinally-extending, spaced-apart, protruding guide funnel lands 32, the lands 32 protruding outwardly from the outer surface 24 of the guide funnel 16. When the guide funnel 16 is disposed in its operative position within the container 12, the lands 32 longitudinally extend therealong the outer surface 24 and abut the inner surface 26 of the container 12 to provide clearance for the guide funnel 16 from the container 12. The lands 32 facilitate the creation of an air shell around the apparatus 10, as shall be more fully described, when the apparatus 10 is disposed within the container 12. As shown in FIG. 5, the guide funnel 16 includes three lands 32 that extend partially down the outer surface 24 terminating at an upper cylindrical portion of the funnel-shaped end 20. More lands could be added to the outer surface 24 of the guide funnel 16 during the machining and manufacturing process, but the three lands 32 of the present invention, equally spaced apart about the outer surface 24, are all that are necessary in order to provide the required clearance between the guide funnel 16 and the inner surface 26 of the container 12.

As illustrated in FIGS. 4 and 5, the apparatus 10 may also include a removably insertable plastic, glass or ceramic insert 34. The insert 34 would be generally cylindrical in order to conform to the tubular passageway 30 of the elongated member 28, and would also include a centrally-located, longitudinally-extending bore 36 through which the embryo 14 and the solution would be conveyed. The insert 34 would also require a means to align and position it within the tubular passageway 30 of the elongated member 28, and would require a means to remove it therefrom. Because of its minute size, perhaps a stereoscopic microscope and various types of microtools would be required to align, position, and remove the insert 34. As shown in FIG. 4, the longitudinally-extending bore 36 of the insert 34 is actually funnel-shaped in order to more efficiently convey the embryo 14 through the bore 36. Depending on the size and the particular stage of the embryo 14 when it is selected for division, the insert 34 may or may not be used.

Figure 2:
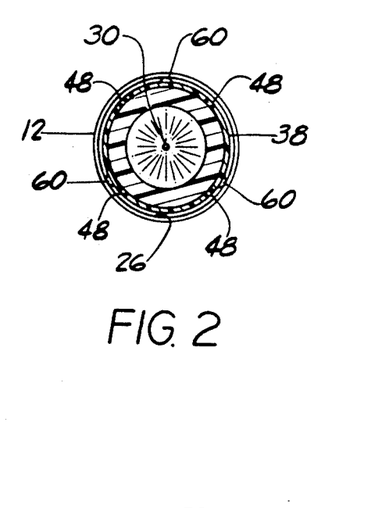
FIG. 2 is a sectional view of the apparatus taken along line 2—2 first shown in FIG. 1.

As shown in FIGS. 1 and 5, the apparatus 10 also includes an elongated, cylindrical central barrel 38 having a first open end 40, an oppositely-disposed second open end 42 which defines a circular rim 44 and an elongated chamber 46 extending from the first open end 40 to the second open end 42. When disposed in its operative position, the upper cylindrical portion of the funnel-shaped end 20 sets within the central barrel 38 adjacent the first open end 40. The central barrel 38 includes a plurality of air holes 48, two of which are shown in FIGS. 1, 2, and 5, which allow air to pass into the chamber 46 in order to facilitate embryo division, which will be more fully described hereinafter. More specifically, the central barrel 38 is adapted for contiguous, sealable placement around the upper cylindrical portion of the funnel-shaped end 20 of the guide funnel 16.

The third piece of the three-piece assembly of the apparatus 10, illustrated in FIGS. 1 and 5, is a generally cylindrical partition cup 50 which, when the cup 50 is disposed in its operative position, is positioned adjacent to the sealed end 13 of the container 12. The cup 50 includes a number of structural elements that ar essential for the embryo dividing process. The general shape or configuration of the cup 50, however, will be first described. The cup 50 includes an inner cup surface 52 and an oppositely-disposed outer cup surface 54, the outer surface 54 being that part of the cup 50 which is positioned adjacent to the sealed end 13 of the container 12. The cup 50 includes a rounded end 56 which is disposed adjacent the sealed end 13 of the container 12 and is shaped so as to conform to the sealed end 13 of the container 12. The cup 50 is further defined by an upwardly-open cup end 58 that opens upward and toward the funnel-shaped end 20 of the guide funnel 16 when both elements are disposed in their operative position within the container 12.

Furthermore, as illustrated in FIG. 5, the cup 50 includes a plurality of spaced-apart, projecting cup lands 60 which protrude from the outer surface 54, and are formed in the machining and manufacturing process. The cup lands 60 are adapted to abut the sealed end 13 of the container 12 in order to provide clearance therefrom when the cup 50 is removably placed into the container 12 adjacent the rounded end 13 of the container 12. The cup 50 includes three projecting cup lands 60, two of which are shown in FIG. 5, which radially converge at the tip of the rounded end 56 of the cup 50. As shown in FIG. 5, the cup lands 60 start approximately halfway down on the outer surface 54 and radially extend downward to convergence at the tip of the cup end 56. When the guide funnel 16, the central barrel 38, and the cup 50 are disposed in their operative position of close-fitting assemblage within the container 12, the lands 32 of the guide funnel 16 and the cup lands 60 should be placed in longitudinal alignment. The projection or protrusion of the funnel lands 32 and the cup lands 60 from their respective surfaces are equal in order to form an evenly spaced clearance from the inner surface 26 of the container 12. As shown in FIGS. 1 and 5, the cup lands 60 start their downward projection from the outer surface 54 at a point coterminous with a circumferentially-extending cup ledge 62. The ledge 62 serves as a seat for the circular rim 44 of the second open end 42 of the central barrel 38 when the cup 50 and the central barrel 38 are disposed within the container 12 for embryo division.

As illustrated in FIGS. 1, 3, and 5, the cup 50 also includes an elongated partition member 64. The partition member 64 is located within and bisects the cup 50. As illustrated in FIGS. 1 and 5, the partition member 64 projects upwardly toward, and in the preferred embodiment past, the cup end 58 a slight distance and also extends downwardly into the cup 50 to the rounded end 56.

Furthermore, the partition member 64 bisects the full diameter of the cup 50 and is attached at opposite sides of the inner surface 52 and also at the rounded end 56. If the cup 50 is manufactured by some plastic molding or forming process, the partition member 64 may be created during one of the plastic forming processes or procedures. Thus, the partition member 64 would be integrally formed and continuously attached therealong opposite sides of the inner surface 52 and to the rounded end 56. If the partition member 64 were formed and attached to the cup 50 in the above-described manner, there would be no seams or joints along the points of attachment wherein, as shall be more fully described hereinafter, the divided embryos could settle. Thus, the partition member 64 would be unitized to the cup 50.

In addition, the partition member 64 could also be manufactured separately from the cup 50 and adapted to be removably inserted therein. The attachment of the partition member 64 to the cup 50 could be by some type of epoxy glue which would not chemically react with the vehicle medium during embryo division. If the partition member 64 were manufactured as a separate piece, the insertion and attachment of the partition member 64 to the inner surface 52 of the cup 50 would still require a seamless fit to prevent the embryo(s) thus divided from settling in joints or fissures along the point of attachment or catching onto burs or ridges that may form by epoxy glue that has seeped out and hardened along the point of attachment to the inner surface 52. The partition member 64 integrally formed to or unitized with the cup 50 may be the more feasible option from a manufacturing standpoint.

As shown in FIGS. 1 and 5, the partition member 64 includes, at the portion thereof that projects upwardly past the cup end 58, an integrally-formed tapered partition edge 66. When the apparatus 10 is disposed in its operative position, the partition edge 66 is located in close proximity (hundredths o thousandths of an inch or metric equivalents) to the elongated member 28 of the funnel-shaped end 20 and directly underneath the tubular passageway 30 of the elongated member 28, as shown in FIGS. 1 and 3. The partition edge 66 extends the diameter of the cup 50 and is coequal in diametric length with the partition member 64. Although in the preferred embodiment of the apparatus 10, as illustrated in FIGS. 1 and 5, the partition edge 66 juts or protrudes above the rim of cup end 58, the partition member 64 can be shortened so that the partition edge 66 is level with the rim of the cup end 58 or slightly beneath it. In order to accommodate such a design, the central barrel 38 would have to be somewhat shortened or the funnel-shaped end 20 and/or the upper cylindrical portion of the guide funnel 16 would have to be lengthened so that the elongated member 28 would still be in close proximity to the tapered edge 66 when the apparatus 10 is disposed in its operative position within the container 12.

In order to divide the embryo 14—or a succession of embryos—in half after exiting the tubular passageway 30 of the elongated member 28, by processes or methods more fully described hereinafter, a severing means must be utilized for dividing the embryo 14, the severing means disposed immediately adjacent and beneath the tubular passageway 30. The severing means may include various elements: ceramic, steel, or glass blades; or microthin elongated wires or filaments manufactured from a specialty steel or steel alloy of high tensile strength. In the apparatus 10 of the present invention, the severing means includes a removably securable cutting edge 68 mounted to the partition edge 66 and adapted to divide the embryo 14 in half immediately after the embryo 14 has exited the tubular passageway 30 of the elongated member 28. As illustrated in FIGS. 1, 3, and 5, the cutting edge 68 may be a blade adapted for removable securement into a longitudinal recess 70 on the partition edge 66. As illustrated in FIG. 5, the recess 70 is centrally positioned on the partition edge 66, and as shown in FIGS. 1 and 3, the cutting edge 68, when it is inserted and secured to the partition edge 66, juts above the edge 66 and the open end 58 of the cup 50 toward the tubular passageway 30.

As was previously mentioned, the cutting edge 68 may be a blade manufactured from ceramic, steel, or glass that has been treated with a sterilizing substance, or adapted for use in a sterile environment, and ground, smoothed, or formed to tolerances at least to the thousandth of an inch and perhaps even greater. When the cutting edge 68 is disposed in its operative position, as illustrated in FIGS. 1 and 3, it must be symmetrically aligned with the tubular passageway 30 of the elongated member 28 so the embryo(s) 14 exiting through the passageway 30 are precisely divided in half by the cutting edge 68. If the alignment of the cutting edge 68 with the tubular passageway 30 were asymmetrical, i.e., shifted one way or another, exact division of the embryo 14 in half would not result.

In order to facilitate the symmetrical and bisectional alignment of the cutting edge 68 with the tubular passageway 30 when the apparatus 10 is disposed in its operative position, adjustments for selectively rotating the cup 50 with respect to its sealable and contiguous placement within the second open end 42 of the central barrel 38 may be required. The adjustments permit the cup 50 to be turned or rotated during and after its sealable and contiguous assembly to the central barrel 38. Slight deformations of the cup 50 that could occur from intensive use may be compensated by adjustably turning or rotating the cup 50 in order to achieve bisectional alignment of the cutting edge 68 with the tubular passageway 30. If slight deformations of the cup 50 or the partition member 64 would occur from intensive use or from damage due to mishandling, thus displacing the alignment of the cutting edge 68, adjustably turning or rotating the cup 50 would realign and center the cutting edge 68 immediately and directly beneath the tubular passageway 30.

In addition to the cutting edge 68, the severing means may include a microthin elongated wire or filament stretched across the diameter of the cup 50 immediately above and adjacent to the partition edge 66. Although not shown in FIGS. 1 through 5, the microthin elongated wire would be positioned parallel to the apex of the partition edge 66 and in close proximity (a distance of hundredths or thousandths of an inch or metric equivalents) to the tubular passageway 30 when the apparatus 10 is disposed in its operative position within the container 12. The microthin wire would require a high degree of tensile strength as it would stretch across the diameter of the cup 50 and attach to opposite sides of the inner cup surface 54 or to the inside of the central barrel 38; at all times, however, the microthin wire would have to be maintained parallel and horizontal with the tapered edge 66 and symmetrically and bisectionally aligned with the tubular passageway 30. The slightest amount of sag in the microthin wire would impair the precise division of the embryo 14 into two halves after the embryo 14 has exited the tubular passageway 30.

As shown in FIGS. 1 and 2, when the apparatus 10 is disposed in its operative position with the cup 50, the central barrel 38, and the guide funnel 16 assembled together for close-fitting, snug, removable placement within the container 12, an air shell between the apparatus 10 and the inner surface 26 of the container 12 is created by the clearance provided by the funnel lands 32 and the cup lands 60. FIG. 2 illustrates the cup lands 60 abutting the inner surface 26 of the container 12 thus providing clearance therebetween for the air shell. More specifically, as illustrated in FIG. 1, the air shell is maintained at the sealed end 13 of the container 12 due to the convergence of the cup lands 60 at the rounded end 56, as shown in FIG. 5. FIG. 2 also illustrates the plurality of spaced-apart air slots 48 circumferentially located thereabout the central barrel 38. The air slots 48 are in air flow communication with the air shell and the elongated chamber 46 of the central barrel 38 and are adapted to allow air flow therebetween. The purpose of the air slots 48 will be more fully described hereinafter. The central barrel 38, as shown in FIGS. 2 and 5, shows two air slots 48, although more could be added.

As shown in FIG. 5, the three structural components of the apparatus 10 are designed to easily press-fit together either external to the container 12 for placement therein, or for press-fit assembly inside the container 12. If the apparatus 10 is assembled within the container 12, the first structural component to be inserted and placed therein is the cup 50. The rounded end 56 of the cup 50 is disposed adjacent to the sealed end 13 of the container 12 and the cup lands 60 provide the clearance between the outer cup surface 54 and the inner surface 26 of the container 12, the clearance therebetween defining the region of the air shell. The next piece to be inserted or placed within the container 12 is the central barrel 38. The central barrel 38 is placed within the container 12 so that the circular rim 44 at the second open end 42 of the central barrel 38 rests upon, and is in contiguous contact with, the cup ledge 62 of the cup 50. In addition, there will be sealable contact between the portion of the central barrel 38 adjacent the second open end 42 and the outer surface 54 adjacent the cup end 58 which the central barrel 38 will contiguously encircle, as shown in FIG. 1. After the central barrel 38 has been placed within the container 12, the guide funnel 16 can then be inserted into the container 12, as illustrated in FIG. 1.

The guide funnel 16 is inserted within the container 12 so that the funnel-shaped end 20 protrudes into the elongated chamber 46 of the central barrel 38, as shown in FIG. 1. As shown in FIGS. 1 and 5, the guide funnel 16 has a circumferential guide funnel ledge 72 which rests upon and is in contiguous contact with an upper rim 74 located at the first open end 40 of the central barrel 38. Moreover, that portion of the guide funnel 16 below the funnel ledge 72 which comprises the upper cylindrical portion of the funnel-shaped end 20 is sealably and contiguously encompassed by the inner barrel surface of the central barrel 38. The funnel lands 32 provide clearance for the guide funnel 16 from the inner surface 26 of the container 12 and, along with the cup lands 60, create the circumjacent air shell between the assembled apparatus 10 and the inner surface 26 of the container 12. The spaced-apart air slots 48 on the central barrel 38 permit air flow communication between the air shell and the elongated chamber 46 of the central barrel 38. In contradistinction, a one-piece assembly, for example, would make replacement of the cutting edge 68, cleaning of the tubular passageway 30, and removal of the embryo 14 difficult, if not impossible, and would impede the proper cleaning and sterilization of the apparatus 10 itself.

When the apparatus 10 is inserted within the container 12, the elongated bore 22 of the guide funnel 16 and the tubular passageway 30 of the elongated member 28 are in axial alignment. It should also be noted, as shown in FIGS. 1 and 5, that the cup 50 is further defined by a pair of oppositely-disposed embryo holding chambers 76 which are located within the cup 50 and formed by the partition member 64 bisecting the cup 50. Each holding chamber 76 extends from the rounded end 56 to the cup end 58 and is separate and isolated from the other holding chamber 76. Each holding chamber 76 is designed to hold or maintain within its area a portion of, and specifically one-half, of the divided embryo 14 after embryo division has occurred. Each holding chamber 76 will be sterilized and also adapted to maintain therein the flushing or saline solution, or other vehicle medium, along with the divided embryo 14.

After the apparatus 10 has been placed within the container 12, the snug, closely-fitting assembly of the guide funnel 16, the central barrel 38, and the cup 50 prevents each piece from being jarred or displaced from its sealable and contiguous placement to each other respective piece. Thus, if a laboratory technician were to move the container 12 with the apparatus 10 inserted therein, such movement to different work stations or laboratory benches would not jar, misalign, or displace the assembled apparatus 10.

Although not shown in any of the drawings, the elongated member 28 may be structurally modified to enhance embryo division. This modification would permit the cutting edge 68 mounted upon the partition edge 66 to jut into the elongated member 28. As illustrated in FIGS. 1 and 5, the elongated member 28 is cylindrical and has a tubular passageway 30 extending therethrough in which the embryo 14 is conveyed during the process of embryo division. The modification would include cutting or incising an oppositely-disposed rectangular-shaped or triangular-shaped slot on the lowest portion of the elongated member 28 adjacent the cutting edge 68. The recessed or incised slots would transversely extend the diameter of the elongated member 28 and permit the cutting edge 68 to extend up into the elongated member 28 and, thus, the embryo 14 would be divided before exiting the tubular passageway 30, and not immediately after exiting the tubular passageway 30 as shown in FIG. 3. This would necessitate precision alignment of the cutting edge 68 with the recessed or incised slot on the elongated member 28 and great care would have to be taken in assembling the apparatus 10 so that the elongated member 28 of the guide funnel 16 would not be inserted and assembled to the central barrel 38 with the recessed or incised slot running transverse to the cutting edge 68. This would result in striking, bending, or breaking the cutting edge 68.

Several different methods or processes of dividing the embryo 14—or a number of embryos successively—may be utilized with the apparatus 10 of the present invention. One method of dividing the embryo 14 is by first placing the apparatus 10 within a container 12 after either external assembly or by assembly within the container 12 as aforedescribed, and then mounting the container 12 within a centrifuge (not shown). Centrifuges come in various sizes and are widely used in medical laboratories, hospital laboratories, doctors' clinics and facilities, and university and industrial research facilities. Variously-sized test tube-like containers may be placed within the centrifuge's cylindrical mounting holes, and the centrifuge rapidly spins either one container or a number of containers, thus producing a centrifugal force for separating substances of different densities, for removing moisture, or for simulating gravitational effects, the most notable simulation of gravitational effects being used by NASA in the training of astronauts.

After the container 12 is mounted in one of the holes in the centrifuge (not shown), with the apparatus 10 already insertably placed within the centrifuge, the embryo(s) 14 maintained within a vehicle medium such as a flushing or saline solution is discharged into the bore 22 of the guide funnel 16. The centrifuge is then turned on (centrifuges may be placed on a tabletop or counter with provision being made to inhibit or prevent vibrations and oscillations during use), and the rapid spinning of the centrifuge subjects the embryo 14 to the centrifugal force propelling and forcing the embryo 14 through the tubular passageway 30 of the elongated member 28. In effect, centrifugation draws the embryo 14 to the bottom of the funnel-shaped end 20 and, in combination with gravitational effects, thence into the tubular passageway 30 of the elongated member 28. With the centrifuge still rapidly spinning, the centrifugal force propels the embryo 14 downward through the tubular passageway 30 of the elongated member 28 and against the cutting edge 66 which is located immediately adjacent the exit end of the tubular passageway 30.

As shown in FIG. 3, the embryo 14 is divided into two equal halves as the embryo 14 exits the passageway 30 and is cut or sliced by the cutting edge 68. Each half of the now-divided embryo, or demi-embryo as it may be called, is further propelled by the centrifugal and gravitational force downward and into each respective holding chamber 76. Thus, each half of the divided embryo is held in each respective holding chamber 76 separate and isolated from the other half-embryo. The centrifuge can then be turned off, and after its spins down, the container 12 may be removed and, in a sterile environment, the apparatus 10 is removed one piece at a time with the last piece, the cup 50, being carefully removed therefrom so that the half-embryo held in each respective holding chamber 76 is not disturbed or introduced to unsterilized elements, such as petri dishes, pipettes, or unsterilized laboratory equipment. A number of embryos may be successively discharged into the bore 22 of the guide funnel 16, and as they are forcefully propelled through the tubular passageway 30, one after another, division by the cutting edge 68 occurs. The rapid spinning of the centrifuge, and the dispersion of the embryos in the saline or flushing solution, prevents the embryos from clogging up the tubular passageway 30 as they are forcefully propelled therethrough.

Another method of dividing the embryo 14 employs what may be called a negative pressure method. A centrifuge is not needed with this method. First, the apparatus 10 is either assembled within the container 12 or assembled externally and then placed within the container 12. The method itself comprises the steps of inserting a hollow elongated tube 78, as illustrated in FIG. 1, the tube 78 being open at both tube ends, through the open end of the container 12 and partially into the container 12 so that one tube end of the tube 78 is in sealable contact with the guide funnel 16 adjacent the open end 18. The diameter of the tube 78 should be smaller than the diameter of the elongated bore 22 to provide an area for trapping air between the tube 78 and the container 12 and to allow snug fitting and contiguous, sealable contact between the tube 78 and the portion of the guide funnel 16 adjacent the open end 18. A generally circular-shaped rubber stopper 80 having an elongated duct 82 longitudinally extending therethrough should then be wedged around that portion of the tube end which protrudes from the container 12 and also wedged against the inner surface 26 adjacent the open container end for providing sealable airtight closure from the atmosphere. The rubber stopper 80 will contiguously encircle that portion of the tube end which protrudes from the container 12 and will also be contiguously wedged against a portion of the inner surface 26 adjacent the open container end. The wedging of the rubber stopper 80 around the tube 78 and against the inner surface 26 of the container 12 creates a pocket of trapped air in the container 12, more specifically, the pocket of trapped air extends from the stopper 80 to the open end 18 of the guide funnel 16.

In addition, as shown in FIG. 1, the longitudinally-extending duct 82 is in flow communication with the air pocket thus created and also in flow communication with the external atmosphere. Thus, the duct 82 is adapted to allow the passage or evacuation of air therethrough. Also utilized is an evacuation line 84 having a first end inserted into the duct 82 formed within the stopper 80. The free second end of the evacuation line 84 can be attached to a compressor (not shown) or it may simply have its free second end covered by a removably sealable stopper (not shown) which can be covered or removed as needed during the embryo dividing process. The first end of the evacuation line 84 will be inserted snugly and securely into the stopper 80 sometime before the actual process of embryo division. With the container 12 securely mounted upon a stand or tray setting upon a laboratory workbench, the next step is to pour the vehicle medium, such as the flushing or saline solution, wherein either the single embryo 14 or a number of embryos are maintained, into the tube 78. The flushing or saline solution maintaining the embryo 14 will flow through the tube 78 and settle temporarily within the area of the elongated bore 22 of the guide funnel 16 adjacent the funnel-shaped end 20. Then the open end of the tube 78 should be sealed by a cover or stopper. Next, the air that has been trapped in the air pocket between the container 12 and the tube 78 is evacuated through the line 84 previously inserted in the duct 82 of the stopper 80. By either removing the removably sealable stopper at the second end of the line 84 or employing a small compressor, the air trapped within the air pocket can be withdrawn and thus negative pressure will be created by the evacuation of the air in the area circumjacent the tube 78 and confined by the container 12. Thus, the embryo 14 is forced through the tubular passageway 30 and against the cutting edge 68 by the sudden change or drop in pressure due to the evacuation of the air.

The embryo 14 is divided in half after it exits the passageway 30 due to the negative pressure created by the sudden withdrawal of the trapped air between the container 12 and the tube 78, and the effects of gravity; each half of the divided embryo, referred to as a half or demi-embryo, then falls into each respective holding chamber 76 where it is held separate and isolated from the other half embryo and yet still maintained within a portion of the flushing or saline solution. After the embryo(s) are divided, the apparatus 10 may be removed from the container 12 whereupon the apparatus 10 is disassembled and each half embryo is removed from each respective holding chamber 76 for eventual implantation into a recipient.

Yet another method of dividing the embryo 14 or a number of embryos is by utilizing an injection or injecting means. The injecting means may employ a hypodermic needle having a plunger and an elongated, microthin tube. For example, the embryo 14 maintained within a flushing or saline solution is drawn into the upper end of the hypodermic needle by suction. Next, the hypodermic needle is placed within the container 12 so that the microthin, elongated tube is aligned with, and contiguous to, the tubular passageway 30 of the elongated member 28. Then, the researcher or laboratory assistant presses down on the plunger, thus forcing the embryo 14 through the microthin tube and discharging the embryo through the tubular passageway 30 and against the cutting edge 68 whereupon the embryo 14 is divided in half. Because of the downward force of the plunger, each half embryo falls into the respective holding chamber 76 after the embryo 14 is divided by the cutting edge 68. As was previously described, the apparatus 10 can then be removed from the container 12, disassembled in a sterile environment, and each half embryo can be removed from each respective holding chamber 76 for further study, experimentation, or implantation in a recipient. If a number of embryos are to be divided, the plunger may need to be depressed a number of times in order to successively force the embryos out of the needle and through the tubular passageway 30.

Figure 6:
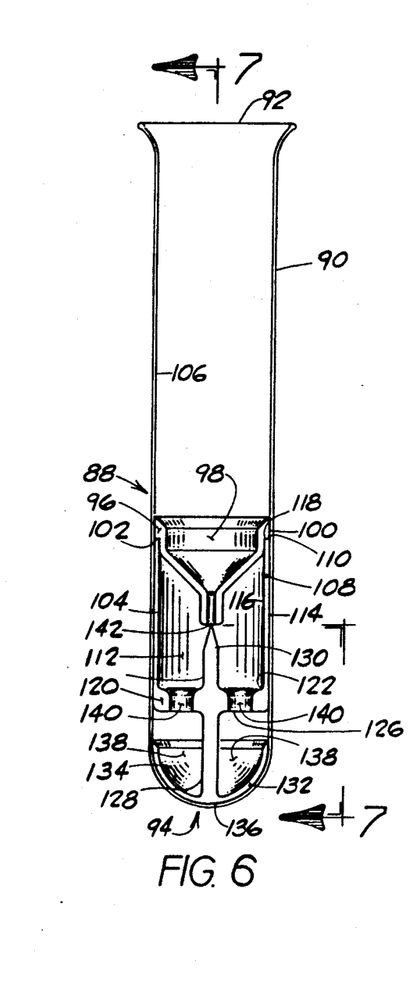
FIG. 6 is a side elevational view of an alternate embodiment of an apparatus constructed in accordance with the present invention.
Figure 7:
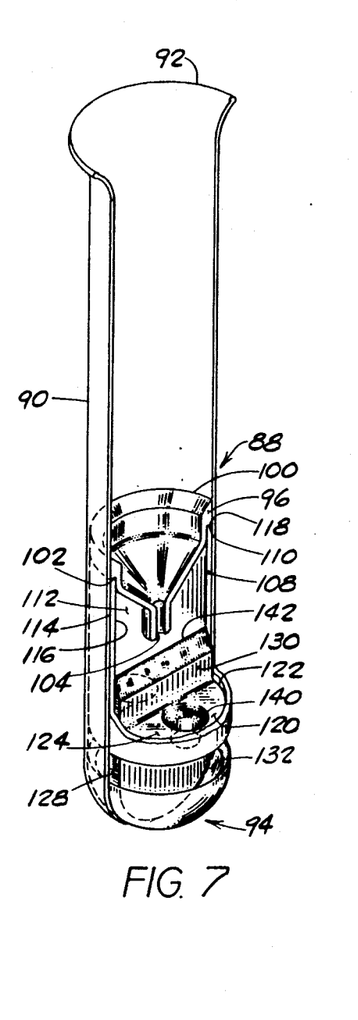
FIG. 7 is a perspective view of the apparatus first shown in FIG. 6 illustrating the disposition of the apparatus within a test tube-like container.
Figure 8:
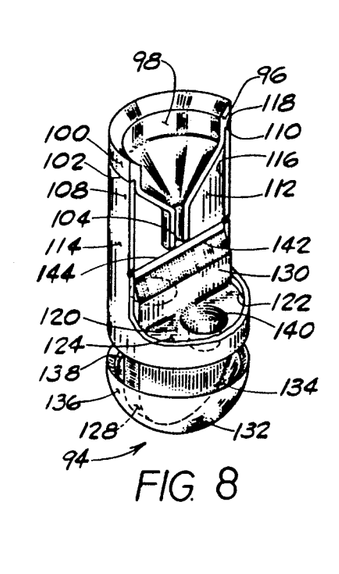
FIG. 8 is a perspective view of the apparatus first shown in FIG. 7 illustrating the structural components of the apparatus when disposed outside of the test tube-like container.

An alternate embodiment of the embryo dividing apparatus is illustrated in FIGS. 6, 7, and 8. The alternate embodiment of the apparatus 88 may be either a one-piece unit or a unitized assembly, but for ease and efficiency in cleaning, repair, and maintenance of the apparatus 88, and, most importantly, for removing the embryo (not shown) after division, the apparatus 88 is a two-piece assembly which is press-fitted together either external to a test tube-like container 90 or is assembled within the container 90. As with the preferred embodiment of the apparatus 10, the alternate embodiment of the apparatus 88 is adapted for dividing one or more embryos, maintained or suspended in a vehicle medium such as a flushing or saline solution. The apparatus 88 is adapted for removable placement or insertion within any of variously-sized test tube-like containers; the container 90 shown in FIGS. 6, 7, and 8 has an upper open end 92 and an opposite rounded sealed end 94, the apparatus 88 when disposed in its operative position is positioned adjacent the rounded sealed end 94 of the container 90.

The apparatus 88 includes a funnel-shaped member 96 having an inner surface 98 and an exterior surface 100, a circumferential exterior lip 102, and an elongated nozzle 104, the nozzle 104 adapted to allow passage therethrough of the vehicle medium and the embryo(s) to be divided. When the funnel-shaped member 96 is disposed in its operative position, a portion of the exterior surface 100 is in contiguous sealable contact with an inner surface 106 of the container 90, as illustrated in FIG. 6. The funnel-shaped member 96 comprises one element of the apparatus 88.

The apparatus 88 also includes an elongated, generally cylindrical member 108 having an open upper end 110, a longitudinally-extending central cavity 112, a circumferential exterior surface 114, and an oppositely-disposed interior surface 116. The exterior surface 114, as illustrated in FIGS. 6 and 7, is in contiguous sealable contact with the inner surface 106 of the container 90 when the cylindrical member 96 is disposed in its operative position within the container 90. The cylindrical member 96 has a circular rim 118 adjacent its open upper end 110 for receiving the lip 102 of the funnel-shaped member 96 when the funnel-shaped member 96 is assembled to the cylindrical member 108 and both elements are placed within the container 90. As shown in FIGS. 6, 7, and 8, the funnel-shaped member 96 and the nozzle 104 extend downwardly into the central cavity 112 when the cylindrical member 108 and the funnel-shaped member 96 are within the container 90. As with the apparatus 10 of the preferred embodiment, the apparatus 88 of the alternate embodiment will most likely be constructed of a durable, molded plastic treated to avoid adverse chemical reactions when in contact with the flushing or saline solution within which the embryos are maintained.

The cylindrical member 108 also includes a circular-shaped disc member 120 disposed opposite the open upper end 110 and having a circumferential edge 122 which is integrally secured in sealable contiguous contact to the interior surface 116 of the cylindrical member 108. As illustrated in FIGS. 7 and 8, the disc member 120 substantially closes off the central cavity 112 of the cylindrical member 108 opposite the open upper end 110. Although it is possible that the disc member 120 could be a separate piece adapted for press-fitting to the interior surface 116 of the cylindrical member 108 along the edge 122, in the alternate embodiment of the apparatus 88 the disc member 120 is integrally attached to the interior surface 116 of the cylindrical member 108. The disc member 120 has an upwardly-facing surface 124 which faces the downwardly-extending nozzle 104 of the funnel-shaped member 96 when the apparatus 88 is disposed in its operative position. Opposite the upwardly-facing disc surface 124 is a downwardly-facing disc surface 126 that faces the rounded sealed end 94 of the container 90, as illustrated in FIGS. 6, 7, and 8, when the apparatus 88 is disposed in its operative position within the container 90. Attached to the downwardly-facing disc surface 126, and extending the diameter of the disc member 120, is a downwardly protruding or projecting, half circle-shaped separator plate 128. When the cylindrical member 108 is disposed in its operative position within the container 90, the separator plate 128 protrudes down into the rounded sealed end 94 of the container 90 and is designed to conform in shape to the curvature or concavity of the rounded sealed end 94.

Mounted on the upwardly-facing disc surface 124, as illustrated in FIGS. 6, 7, and 8, opposite the separator plate 128 and protruding o projecting upwardly toward the funnel-shaped member 96 is a cutter supporting member 130. The supporting member 130 protrudes or projects upwardly from the upwardly-facing disc surface 124 and bisects a portion of the central cavity 112 of the cylindrical member 108. Furthermore, the supporting member 130 is coequal in diametric length with the diameter of the disc member 120 and extends to opposite sides of the interior surface 116 of the cylindrical member 108, whereupon the supporting member 130 is integrally attached to each respective opposite side of the interior surface 116 of the cylindrical member 108. The integral and contiguous attachment of the supporting member 130 to opposite sides of the interior surface 116 assures a sealable, watertight closure. It is possible that the supporting member 130 could be removably mountable or securable to the upwardly-facing disc surface 124, though this may be impracticable due to the small size of the apparatus 88. In addition, the supporting member 130 and the separator plate 128 project from opposite sides of the disc member 120 but are positioned in the same vertical plane. As will be more fully described hereinafter, various kinds of severing means are mounted to the supporting member 130 immediately adjacent and in close proximity (the proximity measured in tenths, hundreds, or thousandths of an inch or equivalent metric measurements) to the funnel nozzle 104 for dividing the embryo(s) in half.

When the apparatus 88 is disposed in its operative position of removable placement within the container 90, located adjacent and contiguous to the sealed end 94 of the container 90 is a half circle-shaped cup member 132. The cup member 132, illustrated in FIGS. 6, 7, and 8, includes an interior concave cup surface 134 and an exterior convex cup surface 136. When the apparatus 88 is disposed within the container 90, the separator plate 128 will project bisectionally into the cup member 132 conforming in shape to the concave surface 134 and will also be in contiguous sealed contact with the interior concave surface 134.

The exterior convex surface 136 of the cup member 132 will be adjacent and contiguous to the sealed end 94 of the container 90. The cup member 132 may be attached by some type of non-reactive adhesive glue (epoxy glue) to that portion of the separator plate 128 which conformably protrudes into the cup member 132 so that contiguous and sealed contact with the interior surface 134 is achieved; or the cup member 132 may be integrally attached to that portion of the protruding separator plate 128 during the plastic molding process. In addition, the cup member 132 may be manufactured as a separate piece and adapted for press-fitting to the separator plate 128. It should be noted in FIGS. 6, 7, and 8 that there is a gap or space between the cup member 132 and the lowest portion of the cylindrical member 108. An alternate design of the cup member 132 would be to have the sides of the cup member 132 extend all the way up for sealable contact with the lowest portion of the cylindrical member 108 adjacent the circumferential edge 122 of the disc member 120.

When the cup member 132 is disposed in its operative position adjacent and contiguous to the sealed end 94 of the container 90 and the cylindrical member 108 is disposed in its operative position with the separator plate 128 projecting in sealable contact down into the cup member 132, a pair of embryo receptacles 138 are defined, one of which is located on either side of the separator plate 128. The embryo receptacles 138 are bounded by the separator plate 128 and that adjacent portion of the interior concave cup surface 134. Each embryo receptacle 138 is adapted to hold a portion of the divided embryo(s); more specifically, one-half of the divided embryo after embryo division has occurred, along with some portion of the flushing or saline solution in which the embryo(s) are maintained.

The disc member 120 also includes a pair of circular embryo passageways 140, one passageway 140 disposed on each side of the supporting member 130, as illustrated in FIGS. 6, 7, and 8, and registering with the central cavity 112 of the cylindrical member 108 and each respective receptacle 138. Each passageway 140 is adapted to receive and allow passage therethrough of a portion of the divided embryo and the flushing solution, and the diameter of each passageway 140 is generally larger than the diameter of the funnel nozzle 104.

Several types of severing means can be utilized for dividing the embryo in half immediately after the embryo has exited the nozzle 104, the severing means being located immediately beneath and in close proximity to the nozzle 104. The distance may be measured in millimeters when consideration is given to the fact that an embryo is between 70 and 150 microns in diameter; thus, the distance of the severing means from the nozzle 104 insures exact and precise division of the embryo(s).

As illustrated in FIGS. 6 and 7, the severing means can include a cutting edge 142 mounted on the supporting member 130 and disposed immediately adjacent and below the nozzle 104, the cutting edge 142 being adapted to cut the embryo in half immediately after the embryo(s) exits the nozzle 104. In the apparatus 88, the cutting edge 142 is integrally formed from the upper portion of the supporting member 130. The cutting edge 142 may be manufactured from stainless steel or it may be hardened ceramic or glass overlaid upon the upper sloping portion of the supporting member 130. As illustrated in FIG. 6, the cutting edge 142 is in the same vertical plane as the separator plate 128 and is positioned to exactly bisect the nozzle 104 when disposed in its operative position so that one-half of the embryo falls into each embryo receptacle 138. Precision alignment of the cutting edge 142 immediately beneath and bisecting the nozzle 104 is essential if proper embryo division is to occur.

As illustrated in FIG. 8, another type of severing means may include a thin (microthin) elongated filament or wire 144. The wire 144 is disposed above the cutting edge 142 of the supporting member 130 and immediately adjacent and below the nozzle 104, the wire 144 being parallel to the supporting member 130 and positioned to exactly bisect or divide the nozzle 104. The wire 144 may be composed of a steel alloy or adapted from a fiber optic cable, but its tensile strength must be such that the wire 144 never sags or bows during the life of its use. Any sag or bow in the wire 144 will obviously cause improper embryo division. The wire 144, as shown in FIG. 8, is attached to opposite sides of the interior surface 116 of the cylindrical member 108 and is adapted to cut the embryo in half immediately after the embryo has exited the nozzle 104.

Utilization of the wire 144 for the severing means may enhance embryo division in the following manner. Embryos are maintained within an outer covering called a zona pellucida, the zona pellucida being an acellular glycoprotein material that forms around the embryo. Depending upon what stage the embryo was in when it was selected for division, the embryo may first have to be removed in a separate and prior procedure from the zona pellucida which surrounds and encloses it, and another zona pellucida, referred to as a zona ghost, would have to be created so that the divided halves of the embryo could be placed within that zona ghost after embryo division. The zona ghost, which is the zona pellucida with the embryo removed therefrom, would be mechanically created subsequent to the splitting or division of the embryo and prior to the transfer of the embryo into that particular zona ghost. It is believed that utilizing the wire 144 would eliminate this step and make embryo division quicker and more efficient.

As the embryo enclosed within the zon pellucida exits the nozzle 104 during embryo division, the wire 144 would divide the embryo in half but because of the cohesive forces of the zona pellucida enclosing the embryo, immediately after division each half-embryo would be re-enclosed by that portion of the respective zona pellucida that has been divided along with the half-embryo. In effect, the wire 144 would cut and divide the embryo in half with a separate zona pellucida reforming around each divided embryo. This would eliminate the need to create a surrogate zona —the zona ghost—before embryo division occurred in which each half embryo would need to be placed after embryo division. The elongated wire of the preferred embodiment in apparatus 10 would also cause the same manner of embryo division.

As with the apparatus 10 of the preferred embodiment, the same methods or processes of dividing an embryo(s) can be employed with the apparatus 88 of the alternate embodiment. The centrifugation method and the negative pressure method can be utilized as well as the injecting means method. Employing the injecting means method for dividing an embryo entails forcefully discharging an embryo(s) through the nozzle 104 of the funnel-shaped member 96 and against the cutting edge 142 or the wire 144 in order to divide the embryo(s) in half. The injecting means would include a syringe (not shown) having a plunger and a portion for holding the vehicle medium, such as the flushing or saline solution containing the embryo(s) and in which the embryo(s) would be suspended, along with a hollow needle adapted for alignment with and insertion into the nozzle 104. For embryo division to occur, pressing the plunger will forcefully discharge the embryo through the hollow needle and into and through the nozzle 104 for cutting and division by the cutting edge 142 or the wire 144. After the desired number of embryos have been divided, the syringe may be removed from the apparatus 88 and the apparatus 88 may be removed from its insertion within the container 90. Removal of each half embryo held within each respective receptacle 138 can then occur.

Although a certain preferred embodiment and an alternate embodiment have been shown and described in detail, it should be understood that various changes and modifications may be made therein without departing from the scope of the appended claims.

I claim:

1. An apparatus for dividing embryos that are maintained in a flushing solution, the apparatus being adapted for removable placement in test tube-like containers of various sizes having an open end and a rounded, sealed end, the apparatus for dividing embryos comprising:

an elongated, cylindrical embryo guide funnel having an open end, an oppositely-disposed, funnel-shaped end, and an elongated bore extending from the open end to the funnel-shaped end, the embryo guide funnel adapted to receive and hold within the bore at least one embryo maintained in the solution;

the funnel-shaped end further defining an elongated member having a tubular passageway which is adapted to receive the embryo from the bore and allow the embryo to pass therethrough, the elongated member projecting downward toward the sealed end of the container when the embryo guide funnel is disposed in its operative position;

an elongated, cylindrical central barrel having a first open end, a second open end, and an elongated chamber extending from the first open end to the second open end, the central barrel adapted for sealable, contiguous placement around the embryo guide funnel adjacent the first open end of the central barrel and the funnel-shaped end of the guide funnel;

a generally cylindrical partition cup having an inner cup surface, an oppositely-disposed outer cup surface, a rounded end disposed adjacent the sealed end of the container, and a cup end that opens toward the funnel-shaped end, the partition cup disposed in the container so that the second open end of the central barrel sealably and contiguously encircles the cup end of the partition cup;

an elongated partition member located within the partition cup and projecting upwardly toward the cup end, the partition member bisecting the partition cup and extending the diameter of the partition cup for attachment at opposite sides of the inner cup surface and at the rounded end;

a pair of embryo-holding chambers located within the partition cup and formed by the partition member bisecting the partition cup, each embryo holding chamber separated and isolated from the other chamber and adapted to hold a portion of the embryo after it is divided;

severing means for dividing the embryo in half after the embryo has exited the tubular passageway of the elongated member, the severing means disposed immediately adjacent and beneath the passageway; and injecting means for discharging the embryos maintained within the solution into and through the passageway of the elongated member for dividing by the severing means.

2. The apparatus of claim 1 wherein the partition member includes a tapered partition edge integrally formed from the partition member, the partition edge located in close proximity to the elongated member of the funnel-shaped end and extending the diameter of the partition cup.

3. The apparatus of claim 2 wherein the severing means includes a cutting edge mounted to the tapered partition edge, the cutting edge adapted to divide the embryo in half immediately after the embryo has exited the passageway of the elongated member.

4. The apparatus of claim 3 wherein the passageway and the elongated bore are in axial alignment when the embryo guide funnel is disposed in its operative position within the container.

5. The apparatus of claim 4 wherein the severing means includes a thin, elongated wire located immediately above, and parallel to, the tapered partition edge and in close proximity to the passageway, the elongated wire extending the diameter of the partition cup and adapted to divide the embryo in half after the embryo has exited the passageway.

6. The apparatus of claim 1 wherein the embryo guide funnel includes a plurality of spaced-apart guide funnel lands protruding outwardly from the embryo guide funnel and longitudinally extending therealong, the protruding lands adapted to abut the container to provide clearance for the embryo guide funnel from the container when the embryo guide funnel is placed therein.

7. The apparatus of claim 6 wherein the partition cup includes a plurality of spaced-apart, projecting cup lands protruding from the outer cup surface, the cup lands adapted to abut the container adjacent the rounded, sealed end to provide clearance for the partition cup from the container when the partition cup is placed therein.

8. The apparatus of claim 7 further comprising an air shell located between the container and the apparatus when the apparatus is disposed within the container, the air shell created by the clearance provided by the guide funnel lands and the cup lands.

9. The apparatus of claim 8 wherein the central barrel includes a plurality of spaced-apart air slots circumferentially located thereabout the central barrel, the air slots in air flow communication with the air shell and the elongated chamber and adapted to allow air flow therebetween.

10. A method of dividing an embryo which comprises the steps of:
placing an embryo dividing apparatus within a container having an open end and a rounded sealed end, the embryo dividing apparatus comprising:
an elongated, cylindrical embryo guide funnel having an open end, an oppositely-disposed, funnel-shaped end, and an elongated bore extending from the open end to the funnel-shaped end;
the funnel-shaped end further defining an elongated member having a tubular passageway;
an elongated, cylindrical barrel having a first open end and a second open end, the central barrel adapted for sealable, contiguous placement around the embryo guide funnel adjacent the first open end;
a generally cylindrical partition cup having an inner cup surface and an oppositely-disposed outer cup surface disposed so that the second open end of the central barrel sealably and contiguously encircles it; and
a partition member, including a tapered partition edge integrally formed therefrom with a cutting edge mounted thereto, located within the partition cup, the partition edge located in close proximity to the elongated member of the funnel-shaped end, and bisecting the partition cup forming a pair of embryo-holding chambers;
inserting a hollow tube, open at both ends, through the open end of the container and partially into the container in sealable contact with the embryo guide funnel adjacent the open end of the embryo guide funnel;
wedging a rubber stopper adjacent the tube end protruding from the container nd against the inner surface adjacent the open container end for providing sealable airtight closure;
pouring at least one embryo maintained within a flushing solution into the hollow tube that has been inserted within the container so that the embryo settles in the area of the elongated bore adjacent the funnel-shaped end of the embryo guide funnel;
evacuating the air that has been trapped between the tube and the container through an evacuation line that has been inserted into the rubber stopper and is in air flow communication with the trapped air;
forcing the embryo through the tubular passageway by the change in pressure caused by the evacuation of the air that was trapped between the tube and the container;
dividing the embryo in half by the cutting edge as the embryo exits the passageway; and
holding each half of the divided embryo in each respective embryo holding chamber so that each half embryo is separate and isolated from the other.

11. A method of dividing an embryo by placing an embryo dividing apparatus within a container, the embryo dividing apparatus comprising:
an elongated, cylindrical embryo guide funnel having an open end, an oppositely-disposed, funnel-shaped end, and an elongated bore extending from the open end to the funnel-shaped end;
the funnel-shaped end further defining an elongated member having a tubular passageway;
an elongated, cylindrical barrel having a first open end and a second open end, the central barrel adapted for sealable, contiguous placement around the embryo guide funnel adjacent the first open end;
a generally cylindrical partition cup having an inner cup surface and an oppositely-disposed outer cup surface disposed so that the second open end of the central barrel sealably and contiguously encircles it; and
a partition member, including a tapered partition edge integrally formed therefrom with a cutting edge mounted thereto, located within the partition cup, the partition edge located in close proximity to the elongated member of the funnel-shaped end, and bisecting the partition cup forming a pair of embryo-holding chambers; and
mounting the container within a centrifuge which comprises the steps of:
discharging the embryo maintained within the flushing solution into the bore of the embryo guide funnel;
rapidly spinning the centrifuge in order to subject the embryo to centrifugal force;
propelling the embryo, by the centrifugal force created by the rapidly spinning centrifuge, through the passageway of the elongated member;
dividing the embryo in half by the cutting edge as the embryo exits the passageway; and
holding each half of the divided embryo in each respective embryo holding chamber so that each half embryo is separate and isolated from the other.

12. An apparatus for dividing embryos which are maintained in a flushing solution, the apparatus adapted for removable placement within a test tube-like container adjacent a rounded sealed end of the container, the embryo dividing apparatus comprising:

an elongated, cylindrical member having an open upper end for receiving the solution with the embryos, a longitudinally-extending central cavity, a circumferential exterior surface, and an oppositely-disposed interior surface, the exterior surface being in contiguous sealable contact with the container when the cylindrical member is disposed in its operative position;

a circular-shaped disc member disposed opposite the open upper end of the cylindrical member, the disc member having a circumferential edge which is integrally secured in sealable contact to the interior surface of the cylindrical member;

a funnel-shaped member disposed adjacent the open upper end of the cylindrical member, the funnel-shaped member including an elongated nozzle adapted to allow passage therethrough of the solution and the embryos;

a half circle-shaped cup member having an interior, concave cup surface and an exterior convex cup surface, the cup member disposed in its operative position so that the exterior cup surface is adjacent and contiguous to the rounded, sealed end of the container;

a half circle-shaped, downwardly-projecting separator plate attached to the disc member and projecting downwardly therefrom, the separator plate adapted to conform in shape to the concave cup surface of the cup member for sealable contact thereto;

a cutter supporting member mounted on the disc member opposite the separator plate and projecting upwardly toward the open upper end of the cylindrical member, the cutter supporting member extending the diameter of the disc member to opposite sides of the interior surface of the cylindrical member for attachment thereto;

the disc member having a pair of circular embryo passageways, one of which is disposed on each side of the cutter supporting member, each embryo passageway adapted to receive and allow passage therethrough of the divided embryo;

a pair of embryo receptacles, one of which is located on each side of the separator plate when the separator plate is disposed in contiguous sealed contact with the interior cup surface of the cup member, each embryo receptacle adapted to hold a portion of the divided embryos; and severing means mounted on the cutter supporting member and in close proximity to the elongated nozzle, the severing means adapted to divide the embryo in half immediately after the embryo has exited the funnel nozzle.

13. The apparatus of claim 12 wherein the severing means includes a cutting edge mounted o the cutter supporting member and disposed immediately adjacent and below the nozzle, the cutting edge adapted to cut the embryo in half as it exits the funnel nozzle.

14. The apparatus of claim 13 wherein the severing means includes a thin, elongated wire disposed parallel to and above the cutter supporting member and immediately adjacent and below the nozzle, the wire attached to opposite sides of the interior surface of the cylindrical member and adapted to cut in half the embryo after the embryo has exited the nozzle.

15. The apparatus of claim 14 further comprising an injecting means for forcefully discharging an embryo through the nozzle of the funnel-shaped member and against the cutting edge in order to divide the embryo in half.

16. The apparatus of claim 15 wherein the injecting means includes a syringe wherein the solution containing the embryo would be held, the syringe having a hollow needle adapted for alignment and insertion within the nozzle of the funnel-shaped member for discharging the embryo through the nozzle and against the cutting edge so that division of the embryo occurs.

* * * * *